United States Patent [19]
Pickard

[11] Patent Number: 4,682,491
[45] Date of Patent: Jul. 28, 1987

[54] APPARATUS AND METHOD FOR TESTING PROSTHETIC HEART VALVES

[76] Inventor: Murphy L. Pickard, 3250 Pierce St., Wheatridge, Colo. 80030

[21] Appl. No.: 830,854

[22] Filed: Feb. 19, 1986

[51] Int. Cl.$^4$ ............................................. G01M 19/00
[52] U.S. Cl. ......................................... 73/37; 73/168; 73/865.6
[58] Field of Search ................. 73/37, 168, 812, 865.6

[56] References Cited

U.S. PATENT DOCUMENTS

| | | | |
|---|---|---|---|
| 4,381,663 | 5/1983 | Swanson | 73/37 |
| 4,450,710 | 5/1984 | Nettekoven | 73/37 |
| 4,546,642 | 10/1984 | Swanson | 73/37 |
| 4,598,579 | 7/1986 | Cummings et al. | 73/37 |

FOREIGN PATENT DOCUMENTS

| | | | |
|---|---|---|---|
| 445432 | 6/1975 | U.S.S.R. | 73/37 |
| 685294 | 9/1979 | U.S.S.R. | 73/432 SD |
| 728864 | 4/1980 | U.S.S.R. | 73/168 |

OTHER PUBLICATIONS

Pickard, M. L. et al., *Computer Managed in Vitro Testing of Ventricular Assist Devices,* In Trans. Am. Soc. Artif. Intern. Organs, vol. XXV, pp. 192-196, 1979.

Primary Examiner—Stewart J. Levy
Assistant Examiner—Joseph W. Roskos
Attorney, Agent, or Firm—Timothy J. Martin

[57] ABSTRACT

An apparatus and method for testing prosthetic heart valves prior to implant in the human body provides a test chamber having a flow channel therethrough and a passageway which receives a mounting fixture for a heart valve. The test chamber is used in a mock circulatory loop with the flow channel being in the loop. Preferably, the test chamber has a transverse passageway that intersects the flow channel, and the mounting fixture advances completely through the test chamber from an insertion location to a disconnect location while a dynamic seal is maintained. Two such test chambers may be used in a mock loop, and the loop is configured with an intake chamber fluidly interconnecting one side of each test chamber, and a restriction chamber fluidly interconnecting the other sides of the test chambers. The restriction chamber is variable, and pressure compensation is provided between each of test chambers and the restriction chamber. A pump cyclically drives a fluid through the loop, and flow meters and pressure sensors monitor the test. A data processor monitors and processes the flow data and controls the pump to create a desired flow waveform. The test can also be visually and optically monitored.

42 Claims, 8 Drawing Figures

_Fig. 1_

_Fig. 3_

APPARATUS AND METHOD FOR TESTING PROSTHETIC HEART VALVES

BACKGROUND OF THE INVENTION

The present invention relates to an apparatus and method for testing prosthetic heart valves under conditions simulating the circulatory system under which the valves are to be used. Accordingly, the present invention is particularly useful for mimicking the human circulatory system so that a heart valve may be placed therein, tested and observed for determining the suitability of the heart valve for actual implantation into the body. Thus, the present invention concerns the construction of a circulatory loop or defining a flow channel which loop includes various means for testing parametric values of the heart valve as well as including novel and non-obvious test chambers which actual mount the heart valve for advancement and orientation in the flow channel.

In recent years, the knowledge and skill of surgeons has dramatically increased in the cardiovascular field so that heart surgery has become somewhat commonplace. Statistically, one of the more common corrective surgical procedures in the pulmonary field replaces damaged or deteriorated auricle or ventricle valves in the human heart. As a result, the medical community demands an increased supply of prosthetic valves for surgical implantation. Accordingly, there is a corresponding need to ensure the reiliability of prosthetic valves before actual implantation, especially since the operation, while common, is nonetheless delicate and stressful on the patient. Accordingly, there is value in knowing the suitability and integrity of a prosthetic valve prior to the start of such surgery.

In the past, most techniques for testing heart valves have been directed to durability or fatigue testing of a single valve to see if the design of the valve suits its intended use. Such durability testing apparatus has been described in U.S. Pat. No. 4,381,663 issued 3 May 1983, and U.S. Pat. No. 4,546,642 issued 15 Oct. 1985, both of which were issued to Swanson. However, with increased demand for heart valves, manufacturers desire to test each heart valve for reliability and integrity rather than simple durability. The production line testing of prosthetic heart valves thus requires a machine capable of creating a proper physiological environment and then acquiring parametric data on the performance of the valve under test. In such a machine it must be possible to quickly and easily insert valves into the flow channel, test the valve and then remove the valve.

In the past, most circulatory simulating systems have included stationary heart valve supporting structures so that use of these devices require an initial draining of the system, the removal of the heart valve support, the positioning of the heart valve support in the mounting fixture and the reassembly of the flow channel with the heart valve in place after which the flow channel is charged with fluid. Understandably, with a complex flow channel, this procedure is extremely time consuming and is thus difficult to implement for production line testing. Indeed, prior art apparatus of the type just described often requires a period of up to thirty minutes to test a heart valve. Another danger resides in this technique, though, since biological heart valves must always be maintained in a moistened condition since the best available valves are constructed of organic tissue. Due to the time involved in draining and recharging the system, there exists the danger that the heart valve might become desiccated. If this occurs during draining the system, it is therefore possible that a valve that actually tested good subsequently becomes degenerate due to the drying out of the tissue during the draining of the system.

In order to eliminate the need for draining, disassembling, reconstructing and recharging the flow channel of prior art devices, one prior art test chamber has been developed as described in U.S. Pat. No. 4,450,710 issued 29 May 1984 to Nettekoven. In this device, a test chamber is provided for insertion into a flow channel with the mounting structure for the prosthetic heart valve comprising a shuttle into which one or two heart valves may be mounted. The shuttle means advances and retracts the heart valve into and out of the fluid flow while maintaining a dynamic seal between the shuttle carriage and the walls of the test chamber. While this patent differs from previous techniques, there still remains the possibility that a heart valve may become desiccated when it is not in position within the flow channel.

Another need resulting from the increased demand for prosthetic heart valves is the maintenance of production line testing of each valve for archival purposes. The value of having a permanent record of parametric test data as well as visual data for each approved valve is readily apparent when considering the increased propensity for malpractice and products liability claims. By production line testing of each prosthetic valve and the maintenance of an archival record thereof, manufacturers will later be able to demonstrate the integrity of a valve implanted in the human body, should such need arise. Further, an advantage of the present apparatus and method not heretofore available is the customizing of the testing procedure to correspond to a specific individual's circulatory system, should various parameter of the patient's pulmonary system be known, such that a specific valve can be tested, in vitro, in a manner that simulates the circulatory environment of the specific patient who will receive the valve. Thus, a valve may be tested under very close operating conditions on an individualized basis rather than under generalized test procedures.

SUMMARY OF THE INVENTION

It is therefore an object of the present invention to provide a new and useful apparatus and method for testing heart valves in a simulated circulatory environment.

It is another object of the present invention to provide a method and apparatus for maintaining archival records of production testing of a heart valve, with this archival record containing both visual and parametric data on the performance of the valve on the test.

It is another object of the present invention to provide a method and apparatus for testing of a prosthetic heart valve under individualized test conditions simulating a specific human circulatory environment into which the valve may be placed.

It is a still further object of the present invention to provide an apparatus and method for callibrating flow and pressure sensors within a simulated circulatory system so that the system may be automatically adjusted by computerized techniques which can lead to non-subjective standardized action of valve testing.

It is yet another object of the present invention to provide a test chamber used in an apparatus for simulating the circulatory environment whereby a prosthetic heart valve may always be maintained in substantial contact with moisturizing fluid while it is advanced through the circulatory loop's flow channel and which allows a valve in the channel to be rotated so that different parametric values can be tested.

Accordingly, the apparatus according to the preferred embodiment of the present invention is primarily formed as a circulatory loop that simulates a circulatory system of the human body. This circulatory loop includes an intake chamber that receives a saline fluid through a fluid inlet under the cyclical action of a pump, the stroke of which acts as a heart beat. The intake chamber has first and second orifices that are in fluid communication, respectively, with first and second test chambers. Each test chamber defines a test portion of the flow channel of the simulated circulatory system and each includes a mounting fixture and is received therein which fixtures has a cavity adapted to secure a prosthetic heart valve. Each mounting fixture is movable in the test chamber to selectively move the mounted heart valve from a passive position out of the flow channel and into the test position interposed in the flow channel while maintaining a dynamic seal through the test chamber. A restriction chamber defines a restrictive portion of the flow channel and has a pair of oppositely positioned restriction chamber flow orifices and means, such as a variable cross-section valve, interpositioned in the flow channel for selectively varying the resistance of the flow of the fluid through the restriction chamber. According to the above, the pump and test chambers operate as one-half of the human heart with the restriction chamber mimicking the capillary system.

Each test chamber is in fluid communication with a respective restriction chamber flow orifice by a conduit means that conducts fluid between restriction chamber flow orifice and the test chamber in a direction depending on the positioning of a prosthetic valve. Since the pump and test chamber may pump more fluid into this circulatory loop on a given pump stroke than the volume of fluid which may be passed by the restriction chamber, fluid pressure compensation chambers are provided as part of the conduit means. A fluid pressure compensation chamber is associated with each conduit between the respective chamber and the restriction chamber and each includes a fluid compensation reservoir having one resilient side wall defined by a diaphram that expands to receive excess fluid. Excess fluid pressure is compensated by means of air pressure on an opposite side of the diaphragm so that the fluid compensation chambers act as the veins and arteries of the human body. Suitable flow measuring elements are provided to measure the velocity and volume of fluid flow through the conduits.

In the preferred embodiment of the present invention, a novel test chamber is employed wherein the test chambers each has a flow channel region extending between a first test chamber orifice and a second test chamber orifice, one of which acts as an intake for the test chamber and the other of which as an outlet for fluid in the test chamber. The test chamber is adapted for insertion into the flow channel and has a passageway extending transversely therethrough which intersects the flow channel region. In the valve mounting fixture is sized for close-fitting, mated engagement in the passageway so that it may slide through the passageway in a sealed relationship with respect to the longitudinal axis of the passageway. The mounting fixture thus may be inserted on an entry opening of the passageway on one side of the test chamber and is slidably advanced completely through the passageway and is removed from the passageway in an exit opening on the opposite side of the test chamber. The mounting chamber includes a cavity extending therethrough which may be inserted into the flow channel and includes structure for mounting and supporting a heart valve to be tested. Preferably, the passageway is circular in cross-section with the mounting fixture being formed as a cylinder that may be selectively rotated to change the operative position of the prosthetic heart valve. A fluid reservoir is located on the entry side of the passageway so that a mounting fixture may be immersed in fluid contained in the reservoir thereby precharging the cavities around the heart valve prior to insertion into the passageway so that undesired air pockets are not introduced into the flow channel when the heart valve is moved into position. Flow shaping members and securring elements are provided within the cavity of the mounting element to secure the heart valve therein.

In order to monitor the flow channel, various sensors are provided in addition to the flow meter noted above. In the preferred embodiment, a pair of pressure sensors are provided for each test chamber so that a pressure sensor is located on each side of the heart valve. These pressure sensors electronically monitor the pressure of the fluid in the flow channel to provide archival data. In addition, these signals may used to automatically control the balancing air pressure for the diaphram of the pressure compensation chambers. Automatic monitors may also be used within the test chamber to monitor the position of the mounting element so that proper registration of the heart valve within the flow channel may be automatically attained. Similarly, a step motor may be used to drive the position of the restriction means in the restriction chamber, and an electronic monitor may output the position of the restriction element for automatic processing. To this end, a computer may be interfaced with the various sensors and pressure regulating devices to automatically control the simulated circuit loop described above.

In order to record archival data, the flow channel on either side of the test chamber is preferably linear and is provided at opposite ends with view ports having lenses to permit visual observation of the opening and closing of the heart valve prothesis in actual operating conditions. Video cameras may be employed so that the visual observation may take place on visual monitors with this visual data being recorded on tape for archival purposes. To this end, also, the computer may overlay textural parametric data onto the video tape with this tape being indexed with a serial number corresponding to the prosthetic valve being tested.

Additional advantages of the present apparatus are obtained by including a waveform generator and a servo amplifier driving a lead screw pump so that the stroke length, duty cycle and other parameters of the cycle may be controllably varied. To this end, individualized parametric data according to a specific individual's circulatory system may be fed into the computer and waveform generator to generate the precise pumping action of an individual's heart. The waveform generator, acting through the servo amp, can cause the pump to precisely mimick this pumping action. The computer may then implement a feedback loop responsive to the data measured from the various pressure and flow sensors so that the circulatory loop fairly accurately simulates an individual's circulatory environment into which a selected prosthetic valve will be placed. To this end also, the preferred mounting elements for the valves may be reversed in position and the parametric values changed, so that each valve performance for both inflow and outflow cardiac portions may be evaluated.

Based on the foregoing, it should be appreciated that the broad form of the method according to the preferred embodiment includes the steps of providing at least one test chamber in the flow channel in a simulated circulatory system whereby fluid may flow through the test chamber with the test chamber including a first transport passageway completely therethrough which intersects the flow channel, and providing a first mounting fixture having a first cavity sized to mount a heart valve for orientation in the flow channel. The method then includes the step of mounting a heart valve in the cavity and advancing the mounting fixture through the passageway from a passive position when the heart valve is out of the flow channel through an entryway into the first passageway so that it may advanced into a test position oriented in the flow channel after which it may be further advanced to a disconnect location for removal of the mounting fixture from the passageway. The method includes the step of maintaining a dynamic seal between the test chamber and the mounting chamber during the slidable movement of the mounting way through the passageway.

The preferred method also includes the steps of measuring the pressure of fluid in the flow channel on either side of the heart valve when the heart valve is in the test position and cyclically driving fluid through the flow channel and then measuring the flow rate of fluid as the heart valve opens and closes. The position of the mounting fixture in the first passageway may be automatically monitored to indicate when the mounting fixture is in the passive, test and disconnect positions.

Preferrably, a pair of test chambers are provided and a second mounting fixture slides through a passageway in the second test chamber and is provided with a cavity that mounts a second heart valve. A plurality of test fixtures may be employed with each of the test chambers so that a stacked array of mounting fixtures may be used so that successive ones of the mounting fixtures are progressively advanced through its associated passageway. The preferred method further includes the step of maintaining each heart valve in a fluid environment as it is passed from the passive to the disconnect position.

In the preferred form of the present invention, a computer interface and control system is provided so that the preferred method is directed toward a simulated circulatory system that has a flow channel containing a test fluid and which includes a selectably adjustable fluid restriction element in the flow channel, a compensation chamber which provides both an excess fluid compensation reservoir and which may be adjusted to selectively apply pressure to the fluid in the flow channel, and that includes a pulsatile pump having a selectable adjusted period, applitude and duty cycle for driving the fluid in a selected waveform through the flow channel. Accordingly, another embodiment of the preferred method includes the step of providing data processing means for automatically monitoring fluid conditions in the flow channel and adjusting the pressure applied by the fluid restriction element and controlling the waveform of the pump. The data process means is loaded with data corresponding to the desired waveform of the fluid flow through the channel and an initial pressure applied by the fluid restriction element is set to an initial pressure. The pump is then activated through the desired waveform according to its duty cycle. The flow rate of fluid through the flow channel adjacent the heart valve is measured to generate flow rate data, and the pressure of the fluid upstream and downstream of the heart valve is measured to generate channel pressure data. The flow rate data and channel pressure data are input into the data processing means and used to calculate the fluid flow and pressure waveform of the fluid through the flow channel. This actual fluid flow and pressure waveform is then compared with the desired waveform to determine waveform error and the resistance of the fluid restriction element is adjusted by the data processing means to proprotionately reduce the waveform error by interrative processing of the flow rate and the channel pressure data to tune the fluid flow and pressure waveform on successive cycles of the pump until the fluid flow and pressure waveform models the desired waveform within predefined error range. This method may include the step of adjusting the pressure applied by the pressure means as part of the step of reducing the waveform error.

Video recording apparatus may be used in this preferred alternate method wherein the method includes the step of monitoring the visual operation of the heart valve and recording the visual data corresponding to the opening and closing of the valve in order to provide an archival record, and the method may include the step of overlaying recorded visual data with the flow rate data and the channel pressure data.

These and other objects of the present invention will become more readily appreciated and understood from a consideration of the following detailed description of the preferred embodiment when taken together with the accompanying drawings, in which:

DETAILED DESCRIPTION OF THE PREFERRED EMBODIMENT

The present invention is directed to an apparatus and method adapted for testing prosthetic heart valves. Preferredly, the present method accomplishes testing prosthetic valves in a manner simulating the circulatory system into which the heart valve is to be used. Thus, the present invention seeks to provide a mechanical analog for the human circulatory system, including the heart, arteries, veins and capillaries so that a prosthetic valve may be tested and observed prior to use in the human body.

Figure 1:
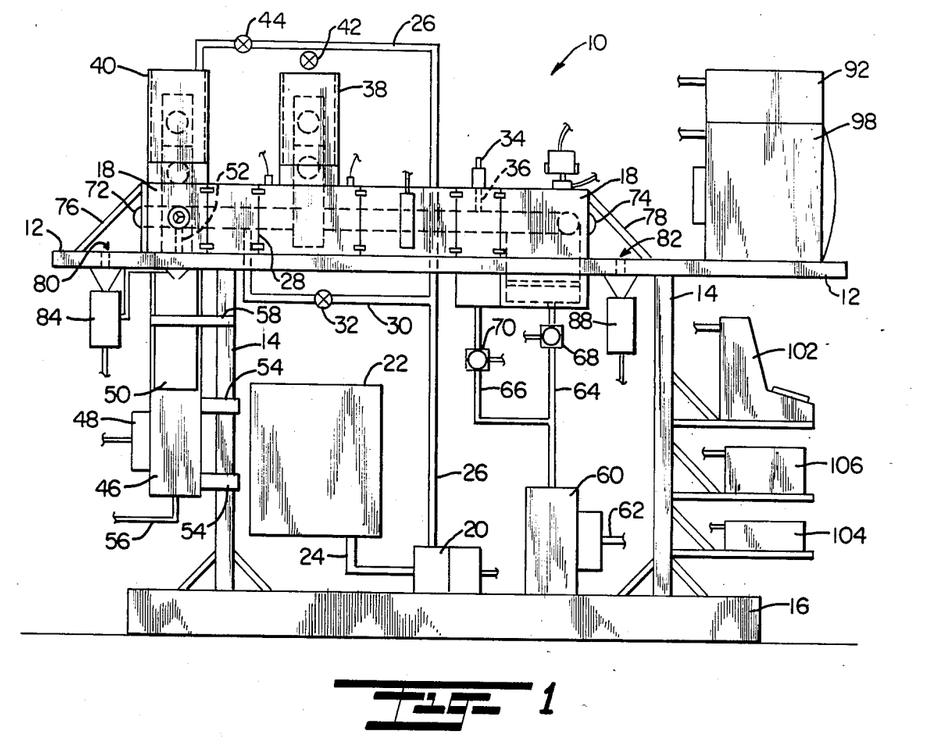
FIG. 1 is a side view in elevation of the apparatus according to the preferred form of the present invention including a circulatory loop and support equipment therefor.
Figure 2:
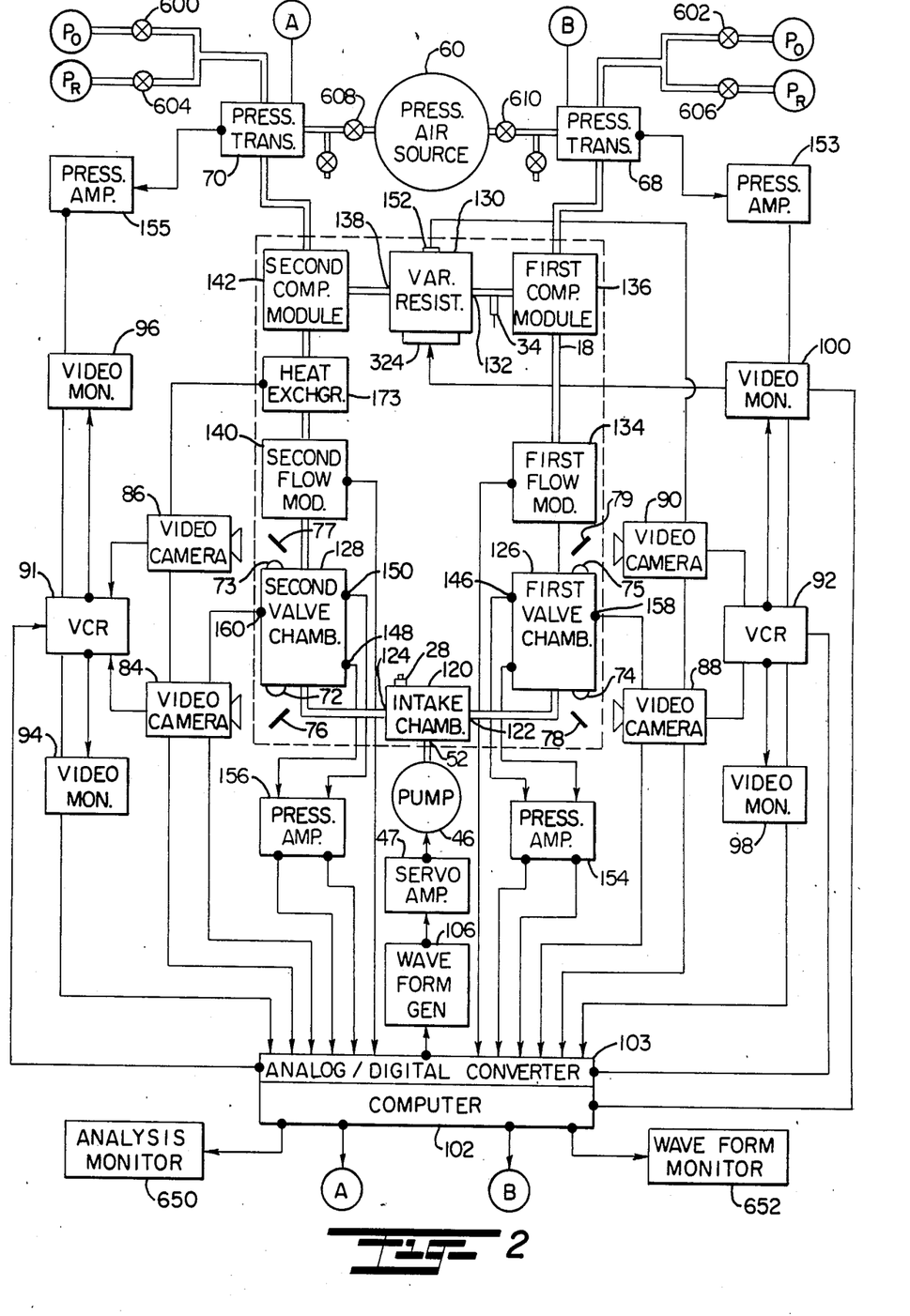
FIG. 2 is a diagramatic view in block form of the preferred form of the present invention.

Certain broad features of the invention are best shown by considering FIGS. 1 and 2 of the drawings together. FIG. 1 shows the mechanical features of the invention, while FIG. 2 shows a block diagram of the heart testing apparatus according to the embodiment of the present invention and which apparatus is used to implement the described method of valve testing. As is shown in FIG. 1, a table 12 supports testing apparatus 10 is on structural uprights 14 fastened to platform 16 which, in turn, may be positioned on a suitable support surface. Apparatus 10 includes a circulatory loop 18 positioned on table 12. Circulatory loop 18 as will be described below, forms a flow path for a circulating fluid, such as saline solution, so that loop 18 mechanically models essential features of the human circulatory system.

In order to provide fluid for the system, fluid pump 20 pumps fluid from reservoir 22 through conduits 24 and 26. Fluid is presented to circulatory loop 18 through conduits 26 and 30 in fluid communication with port 28 of loop 18. A valve 32 is provided to open and shut conduit 30. A bleed valve 34, in the form of a quick release coupling, opens and shuts vent port 36 to allow air to be bled from circulatory loop 18 as it is filled with fluid. Conduit 26 extends upwardly to also allow the filling of first and second test chamber reservoirs 38 and 40 with fluid flow into the test chambers reservoirs being controlled by valves 42 and 44.

Fluid is driven through circulatory loop 18 in a pulsatile or cyclical manner by means of a piston pump 46. A monitor 48 senses the location of the piston in pump 46 for purposes of controlling the volumetric displacement of pump 46. To this end, piston reservoir 50 is filled with fluid which communicates with circulatory loop 18 through an intake opening 52 extending between reservoir 50 and circulatory loop 18. Piston pump 46 is mounted to a support 14 by brackets 54 and is powered by a power source through electrical cord 56. The pump reservoir 50 is also secured to upright 14 by means of a strap bracket 58.

Pressurized air is provided for pressure compensation in loop 18, as discussed more thoroughly below. To provide this air, air compressor 60 is connected to a power source through power cord 62 provides air through conduits 64 and 66 that are controlled by regulator guages 68 and 70, respectively.

In order to monitor the operation of the prosthetic heart valves, various lens ports having suitable optical lenses, such as lenses 72 and 74, are provided for direct visual observation during the testing. In addition, removable mirrors 76 and 78 reflect light through openings 80 and 82 in table 12 so that video cameras, such as video cameras 84 and 88, may transmit a visual signal to an associated video monitor, for example, video monitor 98 shown in FIG. 1. This video signal can also be recorded, by a video recorder 92 and maintained as a permanent, archival record of the valve operation. Computer 102 is provided to control the system, allow any suitable data processing means is within the scope of this invention, and various electronic circuits are provided with power by power supply 104. Waveform generator 106 is used to define the power stroke of pump 46, described in greater detail below. Each of computer 102, power supply 104, and waveform generator 106 are the type generally available through ordinary commercial channels.

As noted above, the mechanical apparatus shown in FIG. 1, can be represented in diagramatic form, as is shown in FIG. 2. In FIG. 2, circulatory loop 18 is shown in greater detail. As shown in FIG. 2, circulatory loop 18 includes an intake chamber 120 that receives fluid from pump 46 from intake opening 52. Intake chamber 120 has a first orifice 122 and a second orifice 124. A first test chamber 126 is in fluid communication with orifice 122, and a second test chamber 128 is in fluid communication with orifice 124. A restriction chamber 130 is located in the flow channel 19 between test chambers 126 and 128 on an opposite flow side of intake chamber 120. Restriction chamber 130 has a first restriction chamber flow orifice 132 is in fluid communication with first test chamber 126 by conduit means formed by first flow module 134 and first compliance module 136. Likewise, restriction chamber 130 has a second restriction chamber flow orifice 138 that is in fluid communication with second valve chamber 128 through a second conduit means defined by second flow module 140 and second compliance module 142.

As is shown in FIG. 2, first test chamber 126 includes a pair of pressure sensors 144 and 146 that send signals through pressure amplifiers 154 to analog/digital converter 103 of computer 102. As is discussed below, pressure sensors 144 and 146 are on opposite sides of a heart valve to be tested in first test chamber 126. Similarly, second test chamber 128 includes pressure sensors 148 and 150 which are located on opposite sides of a second heart valve to be tested, and pressure sensors 148 and 150 send signals through pressure amplifier 156 to analog/digital converter 103. Signals corresponding to fluid flow velocity are likewise transmitted to analog/digital converter 103 from first flow module 134 and second flow module 140, and the amount of resistance in restriction chamber 130 is received by analog/digital converter 103 from resistance monitor 152.

As discussed below, compensation modules 136 and 142 operate on air pressure associated with a diaphram contacting fluid in the circulatory loop. In order to monitor the pressure, pressure amplifier 153 receives a pressure signal from pressure transducer 68 and presents the signal to analog/digital converter 103. Pressure amp 155 receives a pressure signal from pressure transducer 70 and presents this signal to analog/digital converter 103 in order to monitor the air pressure on second compliance module 142. Finally, the existance of test positions for prosthetic valves in first and second test chambers 126 and 128 are signalled to analog/digital converter by position sensors 158 and 160, respectively.

Figure 3:
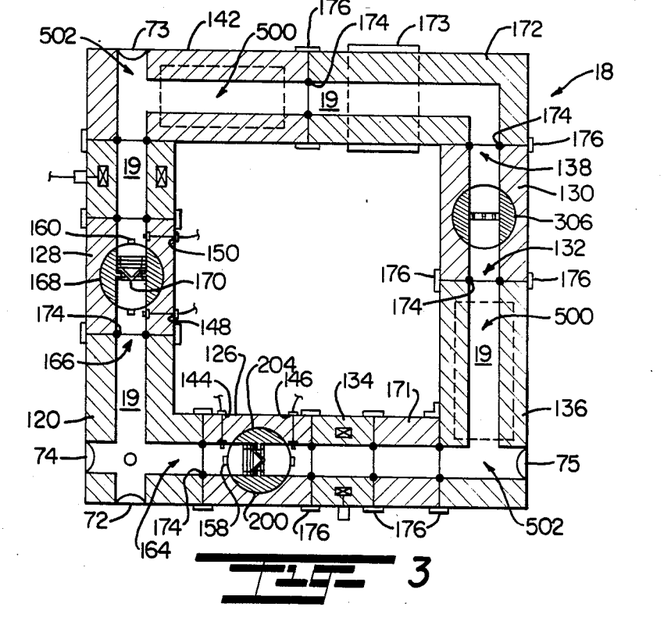
FIG. 3 is a top view and cross-section of a circulatory loop according to the preferred embodiment of the present invention as is shown in FIG. 1.

Before turning to an explanation of the operation of this system as is shown in FIG. 2, it is helpful to consider the structure of circulatory loop 18 as is shown in FIG. 3, and the construction of the components of circulatory loop 18 as is shown in FIGS. 4–8.

Turning first to FIG. 3, it is shown the circulatory loop 18 forms a closed-loop flow channel 19 that is designed to simulate the human circulatory system. Accordingly, intake chamber 120 receives fluid from cylindrical pump 46 (shown in FIG. 1) with this fluid being disbursed towards first and second intake orifices 164 and 166. A first test chamber 126 is shown in fluid communication with intake orifice 164, and includes a first mounting fixture 204 for positioning a first heart valve 200 in the flow path of circulatory loop 18. First test chamber 126 includes a pair of pressure sensors 144 and 146 mounted on opposite flow sides of heart valve 200 so that a pair of pressure signals may be generated to correspond to the pressure of a fluid therein. Position sensor 158 monitors the transverse position of first mounting fixture 204 in order to monitor the orientation of heart vlave 200 accurate position it in the flow channel 19. Similarly, a second test chamber 128 is in fluid communication with second intake orifice 166 and has a second mounting fixture 168 that supports a second heart valve 170 in flow channel 19. A pair of pressure sensors 148 and 150 are again located on opposite sides of heart valve 170 in the flow channel for measuring the pressure of fluid therein. A second position sensor 160 monitors the positioning of second mounting fixture 168 to indicate alignment of second heart valve 170 in the flow channel.

A restriction chamber 130 defines a restrictive portion of the flow path of the circulatory loop 18 and has first and second restriction chamber flow orifices 132 and 138. As will be described with respect to FIG. 6, restriction chamber 130 includes a variable valve element 306 which may be mechanically driven to present different flow cross-sections for the flow path thereby varying the resistance of flow chamber 130 to fluid flow. First flow monitor chamber 134, first transisition chamber 171 and first compensation module 136 define first conduit means as part of flow channel 19 fluidly interconnecting the first restriction chamber flow orifice 132 and first test chamber 126. Similarly, second flow monitor chamber 140, second compensation module 142, and second transisition chamber 172 form a second conduit means fluidly interconnecting a second restriction chamber flow orifice 138 and second test chamber 128. Heat exchanger 173 is associated with transition chamber 172 to monitor and maintain a desired temperature for fluid in flow channel 19.

It should be appreciated that the various component parts of circulatory loop 18 should be constructed out of corrosive proof materials and may be manufactured as modules that may be connected and sealed together by a plurality of O-rings 174 with the various modules being held together by mating clasp elements 176. While, in the preferred embodiment, these elements are constructed of transparent plastic having longitudinal bores therethrough to define the flow channel 19, with the diameter of the flow pattern being approximately 3.75 centimeters, modifications to this construction could certainly be made by the ordinarily skilled person in the art. It should further be appreciated that lenses 74 and 75 are positioned linearly with heart valve 206 so that heart valve 206 may be visually observed therethrough. Likewise, lenses 72 and 73 are linearly aligned with heart valve 170 to permit visual observation of its operation as fluid flows through the valve.

Figure 4:
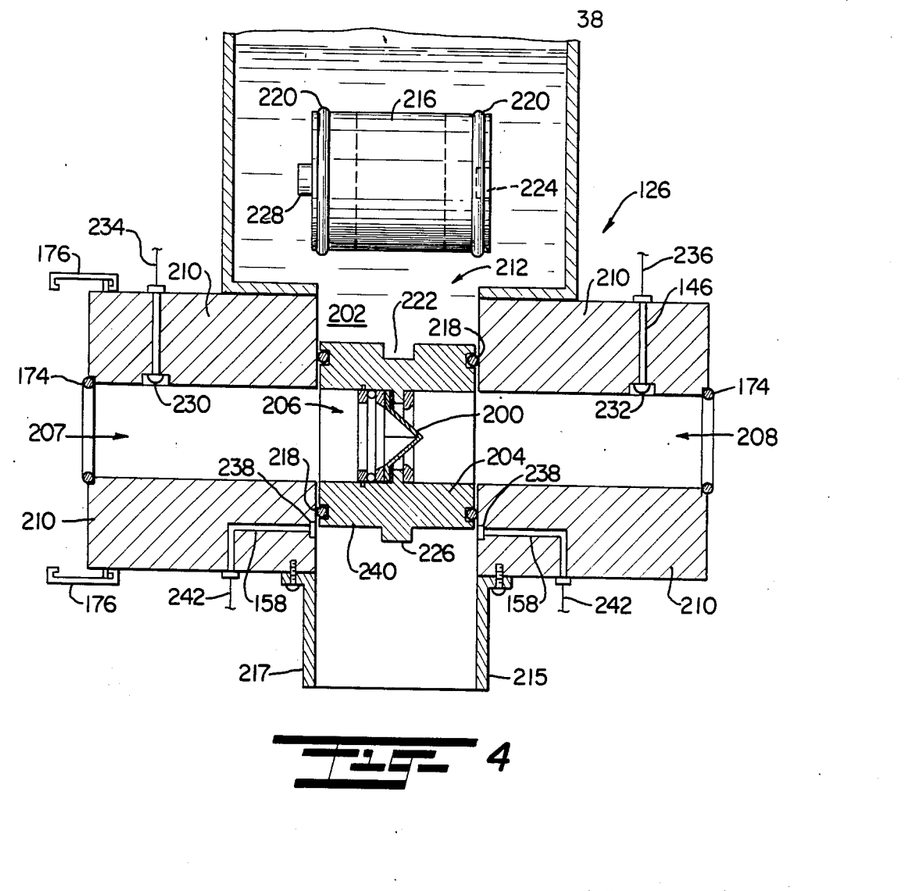
FIG. 4 is a cross-sectional view of the test chamber and mounting element according to the preferred embodiment of the present invention for advancing a prosthetic heart valve into the flow channel.

The construction of the first and second test chambers is the same as is respresentively shown by first test chamber 126 shown in cross-section in FIG. 4. In this figure, heart valve 200 is shown supported in first mounting element 204 and located in a first test portion 108 of the flow channel. First test chamber 126 preferably has a square cross-section through which a cylindrical passageway or bore 202 is transversely formed, with bore 202 diametrically intersecting the longitudinal bore forming first test portion 208 that is also circular in cross-section. Mounting fixture 204 is cylindrical in shape and is sized for close-fitting, mated insertion in and passage through transverse bore 202. Mounting fixture 204 has a diametric bore 206 that has a diameter approximately the same as the diameter of bore 208 so that, when heart valve 200 is positioned in the flow path, bores 207, 206 and 208 form a first test portion of the flow path of circulatory loop 18. Test chamber 126 has a surrounding side wall 210 that has a thickness greater than the diameter of bore 206 so that, as mounting fixture 204 is slid through entry port 212 to exit port 214 of bore 202, fluid in bores 207 and 208 may not escape around side wall 210.

Since it is important to maintain the heart valves tested by the present apparatus in constant fluid contact so that their integrity is not diminished by deseccation, a first reservoir 38 is mounted on top of first test chamber 126 and has a circular opening defining entryway or mouth 212 of passageway 202. Reservoir 38 contains fluid so that one or more additional mounting fixtures, such as fixture 216 may be positioned in the reservoir and pre-charged with fluid prior to their being moved through bore 202. Further, in order to maintain a fluid seal, each mounting fixture is provided with a pair of O-rings adjacent its ends, such as O rings 218 on mounting fixture 204, and O rings 220 on mounting fixture 216. It has been found suitable to construct the mounting fixtures with a diameter of 2.507 inches, with bore 202 having a diameter of 2.510 inches, so that there is approximately 0.003 inch clearance. Because of this reduced clearance, each fixture is coated with a vacuum grease, such as a silicon grease, so that the sliding motion of each mounting fixture may be facilitated as it passes through bore 202. The use of this vacuum grease further helps prevent leakage of fluid circumferentially around the mounting fixtures when they are positioned with their associated heart valve oriented in the flow path. To this end, also, a fixture guide 215 is located at a disconnect location and is secured to test chamber 126 opposite reservoir 38 to receive each mounting fixture 204 as it slides out of bore 202. Guide 215 is a cylindrical sheet so that its surrounding sidewall 217 maintains a fluid seal for cavity 206, thereby maintaining a fluid environment for valve 200.

As discussed below, it is helpful to reverse the position of each of the heart valves. To this end, each mounting fixture is cylindrical in shape so that it may be rotated within the test chamber bore. To enable ease of rotation, each mounting fixture is provided with a square shaped cavity, such as cavity 222 and cavity 224 on fixtures 204 and 216, respectively. Each mounting fixture is then provided with a locking nub that is configured to be received in the cavity of an adjacent mounting fixture, with nubs 226 and 228 of fixtures 204 and 216, respectively, being shown in FIG. 4. Thus, as the mounting fixtures are progressively advanced through the test chamber bore, it should be appreciated that a mounting fixture such as mounting fixture 216 may trail fixture 204 with nub 228 locked into cavity 222 of fixture 204. Thus, fixture 216 may be manually rotated or, if automation is desired, mechanically rotated, to rotate fixture 204 in bore 202. Thus, each mounting fixture may be moved from a passive position wherein its heart valve is outside of the flow path, through a test position aligned in the flow path, and to a removable position wherein a leading mounting fixture is moved out of exit mouth 214 by downward force on the trailing fixture.

As is shown in FIG. 4, in greater detail, each of pressure sensors 144 and 146 include transducers 230 and 232, respectively which are positioned to be in fluid contact with the flow path so that pressure signals may be generated on leads 234 and 236. Similarly, sensors 158 include reflective photosensors 238 which sense a leading edge of the mounting fixture, such as leading edge 240 of fixture 204 so that, when leading edge 240 contacts photosensors 238, heart valve 200 is aligned and this alignment is indicated by a signal on leads, such as leads 242.

Figure 5:
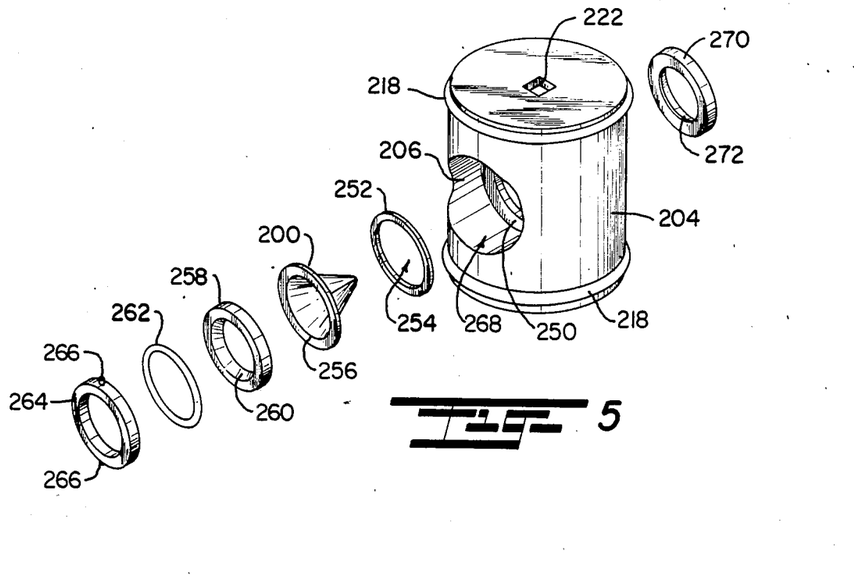
FIG. 5 is an exploded view of the mounting element which holds the prosthetic heart valve according to the preferred embodiment of the present invention.

The mounting of a heart valve, such as heart valve 200, in a mounting fixture, such as mounting fixture 204, is shown in greater detail in FIG. 5. Here, it should be appreciated that diametric bore 206 includes an inwardly projecting shoulder 250. A first valve sizer 252 is mounted against one side of shoulder 250 so that an opening 254 matches the diameter of the heart valve to be tested. Heart valve 200 is then inserted through opening 254 so that its surrounding flange 256 abuts valve sizer 252. An inflow shaper 258 is then mounted against flange 256 with inflow shaper 258 having a converging inner wall 260 that shapes the flow pattern to a desired configuration for the specific heart valve. A rubber compression O-ring 262 is then mounted against inflow shaper 258 and is locked into positon by a valve retainer 264. To this end, valve retainer 264 includes a plurality of locking fingers 266 that may be received in slots, such as slot 268 in mounting fixture 204. An outflow shaper 270 is provided to configure the flow path after fluid is passed through the heart valve without flow shaper 270 having tapered side wall 272 similar to inflow shaper side wall 260.

Figure 6:
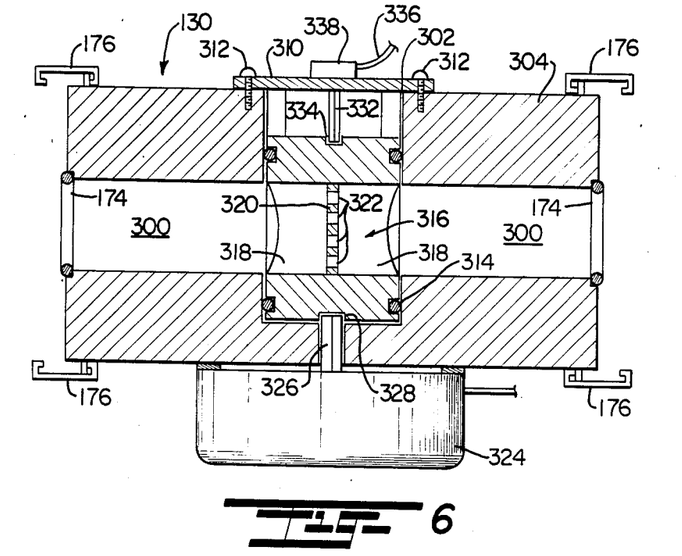
FIG. 6 is a view in partial cross-section showing the restriction chamber used in the circulatory loop of FIG. 3.

Restriction chamber 120 is best shown in FIG. 6 and is formed by a square shaped block of plastic which a longitudinal circular bore 300 is formed. A transverse bore 302 of larger cross-section is then formed partially through side wall 304 of chamber 130 so that bore 302 diametrically intersects bore 300. A cylindrically shaped valve element 306 may then be placed in bore 302 and held in position by a spacer ring 308 and a mounting plate 310 that is held onto side wall 304 by a pair of mounting screws 312. A fluid seal is provided at opposite ends of element 306 by means of a pair of O-rings 314 so that valve element 306 may be rotated in bore 302. Valve element 306 has a diametric bore 316 having a diameter corresponding to the diameter of bore 300, with bore 316 being provided diametrically of valve element 306. Bore 316 has divergent side walls 318 so that, as valve element 306 is rotated in bore 302, a substantially uniform cross-section for the flow path through bore 300 and bore 316 is maintained. To this end, it should be appreciated that bore 300 and bore 316 provide a restrictive portion of the flow path though circulatory loop 18.

The purpose of restriction chamber 130 is to provide resistance to the flow of fluid, which resistance corresponds to the capillaries in the human circulatory system. To this end, a restriction element 320 is mounted in bore 316 to present a blockage to flow through the flow path. Restriction element 320 is provided with a plurality of ports 322 which may be varied in size, if desired. However, in order to provide variation in resistance to fluid flow, a motor 324 is provided to rotate element 320. Motor 324 has a square shaped shaft 326 which is received in a square shaped opening 328 at one end of valve element 306 so that, as shaft 326 turns, valve element 306 is rotated so that restriction element 320 varies the effective flow cross-section for the restrictive flow path through restriction chamber 130. Motor 324 is preferably a step motor controlled by computer 102. In order to monitor the rotational position of valve element 306, a rotation sensor, such as a potentiometer 338, is driven by its shaft 332 that is received in cavity 334 that has a corresponding shape to the cross-section of shaft 332. Thus, electrical lead 336 measures the change in resistance of potentiometer 334 so that the position of valve element 306, and and thus restriction element 320, may be electrically monitored. Naturally, other rotational sensors could be used in place of potentiometer 334.

Figure 7:
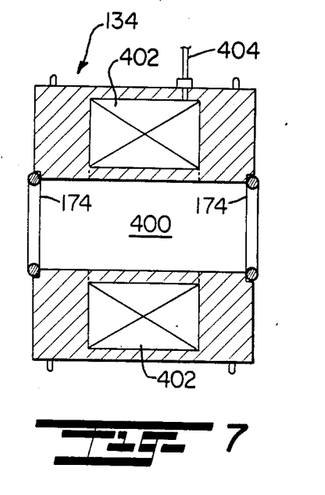
FIG. 7 is a cross-sectional view of a flow sensor chamber used in the circulatory loop of FIG. 3.

A cross-section of the flow chambers used in circulatory loop 18 is shown in FIG. 7 wherein representative flow chamber 134 is formed out of a block of non-magnetic, corrosive resistant material having a longitudinal bore 400 formed therein to define a flow meter portion of the flow path of circulatory loop 18. A non-intrusive flow sensing element, such as a electromagnetic flow probe 402 surrounds bore 400 and is connected to an electrical lead 404 which measures the Faraday potential of an ionic fluid which passes through bore 400. Since the fluid selected for circulatory loop 18 is a saline solution that corresponds to human electrolyte, this saline solution is highly ionic. Thus, the Faraday potential varies with the volumetric flow of the saline solution. The flow monitor device is a commercially available unit available from Carolina Medical Electronics, Inc. of King, N.C.

Figure 8:
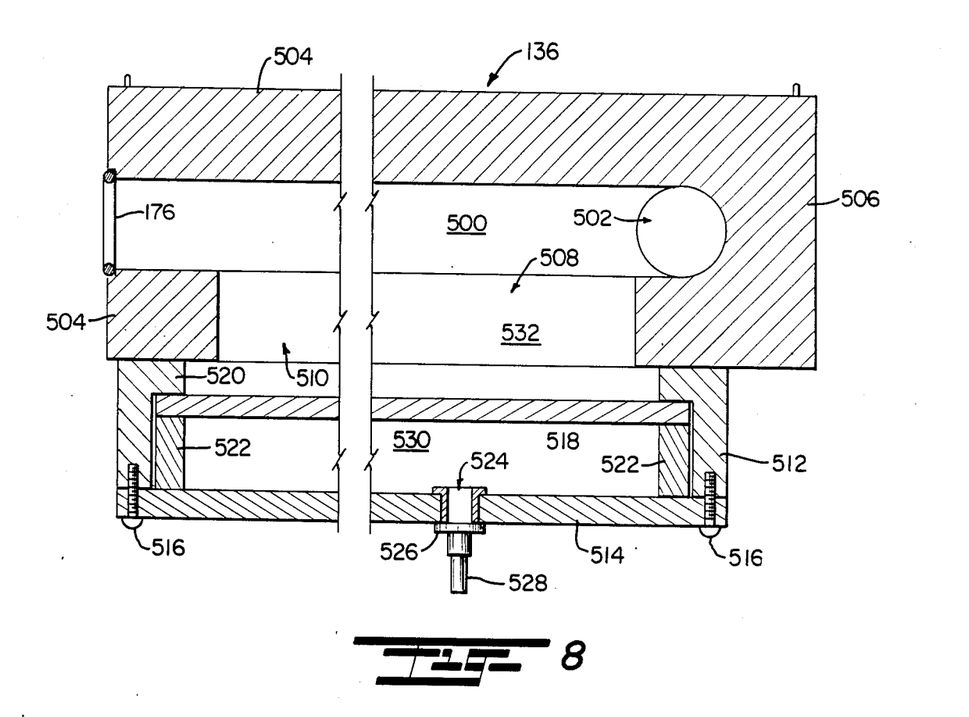
FIG. 8 is a view in cross-section of a compliance chamber used in the circulatory loop of FIG. 3.

The final representative module for circulatory loop 18 is shown in cross-section in FIG. 8 wherein compensation module 136 is shown in cross-section. It should be appreciated that compensation module 142 is the same as module 136. Here, a longitudinal bore 500 is cut almost completely through the length of a block of plastic with bore 500 having the diameter common with remaining flow path bores. This longitudinal bore, at its end, is intersected by a transverse bore 502 which provides a right angle coupling to another module and also which provides a mounting region for one of the lense ports, such as lense port 75. Accordingly, compensation module 136 has a surrounding side wall 504 and an end wall 506. An enlarged rectangular opening 508 is formed through one side of side wall 504 to define a storage reservoir for fluid that is being circulated by pump 46 through the flow path. To this end, mouth 510 of opening 508 is surrounded by a rectangular upstanding wall 512 that is then enclosed by a cover plate 514 held in position by mounting screws 516. It should be appreciated that surrounding wall 512 and plate 514 both fluidly and hermetically seal opening 508. In order to provide compliance, a resilient diaphram 518, formed out of polyurethane, extends across inwardly projecting shoulder 520 of surrounding wall 512 and is held into a fluid and hermetic seal against shoulder 520 by spacer ring 522 that is held in position between the peripheral edge of diaphram 518 and mounting plate 514. The air inlet port 524 is formed through a central portion of retaining plate 514 and a releasable gas coupling 526 is mounted thereto so that air hose 528 may be coupled, in a quick release manner, in gas communication with air chamber 530 formed between diaphram 518 and retaining plate 514. Accordingly, it should be appreciated that a fluid chamber 532 is formed by bores 500, 502, opening 508 and the open area betwen diaphram 518 and side wall 504, while an air chamber 530 is located on the opposite side of diaphram 518. Thus, pressure may be exerted on fluid in the flow path by varying the air pressure in air chamber 530 so that diaphram 518 is flexed against the resistance provided by the fluid in chamber 532.

The operation of the device according to the preferred embodiment of the present invention can now be appreciated with greater clarity and with particular emphasis on FIGS. 1, 2 and 3. As is shown in those figures, the heart valve testing apparatus is first calibrated for air pressure by opening solenoids 600 and 602 to atmosphere so that pressure amps 153 and 155 may have a zero pressure setting. After the zero point for the pressure amplifiers is set, solenoid valves 600 and 602 are closed and valves 604 and 606 are opened to a reference pressure $P_R$, and pressure amps 153 and 155 are set the known reference pressure. This calibrates the pressure readings of the pressure amplifiers so that, after they are calibrated, valves 604 and 606 are closed. At this point, valves 608 and 610 are opened to allow pressurized air from air source 60 to be passed by pressure transducers 68 and 70 to first and second compensation modules 136 and 142, respectively. First and second flow monitors 134 and 140 are calibrated for zero flow for circulatory loop 18. To this end, circulatory loop 18 has been fully charged with fluid through inlet 28, with gas in the system being bled off through gas vent 34.

After all calibrations have been complete, prosthetic heart valves may be mounted in respective mounting fixtures and placed in flow channel 19 of circulatory loop 18 in first and second test chambers 126 and 128. This is accomplished by placing each heart valve in its associated mounting fixture and charging its associated cavity with fluid through reservoirs 38 and 40 so that, when the mounting fixtures are slid into their respective test chambers, the cavities do not introduce gas into the flow channel 19 and so that the heart valves are maintained in a constant fluid environment. Once the heart valves are positioned in the flow channel, the computer 102, which has been loaded with an initial fluid resistance value to be applied by the fluid restriction element and with data corresponding to a desired waveform for fluid flow through the flow channel, pump 46 is activated by computer 102 through waveform generator 106 which presents the desired waveform to pump 46 through servo amplifier 47 so that pump 46 is activated through the desired waveform according to the duty cycle of pump 46. Fluid is then moved from pump 46 into intake chamber 120.

It should be appreciated that the rotational orientation of the heart valves in first and second test chambers 126 and 128 define the direction of fluid flow in flow channel 19. To this end, it is desired that, in one test orientation, a heart valve in test chamber 126 would be open so that flow may take place from orifice 122 toward variable resistance element 132, while the other heart valve in second test chamber 128 would be open for flow from resistance toward intake orifice 124. In their reversed position, both of these heart valves would be rotated 180° for opposite flow. Accordingly, in the first flow position, fluid flows out of intake chamber 120 and through first test chamber 126 according to the selected waveform. Since restriction element 132 does not allow the passage of fluid as rapidly as it is driven by the power stroke of pump 46, excess fluid is received in first compensation module 136 under compliance pressure from diaphram 518 that is controlled by air pressure through hose 528. During the recovery strokes, the excess fluid in first compensation chamber 136 passes through resistance element 132, through second compensation chamber 142 so it may pass through the heart valve in second test chamber 128 and be returned into intake chamber 120 and pump 46 through intake orifice 124. Accordingly, it is important that the variable resistance of resistance element 132 be set so that the volume of fluid flowing through the resistance element over one cycle of the pump equals the volume of fluid pumped by pump 46 in its power stroke. This pumping cycle is then repeated.

For successive pumping cycles, computer 102 monitors the flow rates of fluid at first flow monitor 134 and second flow monitor 140. The computer also monitors the pressures on either side of each heart valve through pressure sensors 144, 146, 148 and 150. The computer first uses interative processing of the flow rate and channel pressure data to calculate the actual fluid flow and pressure waveform through the flow channel to compare this waveform to the desired waveform and generate waveform error data according thereto. The computer may then automatically adjust the resistance of the fluid restriction element and the air pressures in the compensation chambers to tune the fluid fluid flow and pressure waveform on successive cycles of the pump until the fluid flow and pressure waveform models the desired waveform within a predefined error range. Data and waveform may be displayed on analysis monitor 650 or waveform monitor 652.

At such time that the fluid flow and pressure waveform through the flow channel falls within the predefined error range, the computer then utilizes the flow rate data and the channel pressure data to calculate various heart valve parameters as in known in the art. During this time, the computer may activate the various video cameras 84, 86, 88 and 90 to record on video recorders 91 and 92 visual data corresponding to the actual mechanical operation of the heart valves that are being tested. If desired, the computer may overlay the recorded visual data with the actual flow rate and channel pressure data to generate a permanent record.

After testing a pair of heart valves in the above described manner, the heart valves may each be rotated 180° should it be desired that additional test data for both inflow and outflow be checked. This rotation may be accomplished by having additional mounting fixtures in a stacked array above the mounting fixture in each of the first and second test chambers with each stack of mounting fixtures being ganged together for common rotation. Each stack of fixtures may be rotated either manually or, if provided, automatically. When it is desired to remove the heart valves that are being tested, the stacked array of fixtures may be moved downwardly so that each mounting fixture containing the heart valves that have been tested move into the disconnect location within fixture guide 215. If the successive fixtures contain heart valves, the calibration process for the channel flow may again be employed so that the computer again models the waveform before taking the test data. During this time the heart valves in the mounting fixtures located within each channel guide 215 are maintained in a fluid environment so that they may be conveniently removed during a subsequent testing operation.

Based on the foregoing, it should be appreciated that the preferred method according to the preferred embodiment includes the steps of providing at least one test chamber in the flow channel in a simulated circulatory system whereby fluid may flow through the test chamber with the test chamber including a first transport passageway completely therethrough which intersects the flow channel, and providing a first mounting fixture having a first cavity sized to mount a heart valve for orientation in the flow channel. The method then includes the step of mounting a heart valve in the cavity and advancing the mounting fixture through the passageway from a passive position when the heart valve is out of the flow channel through an entryway into the first passageway so that it may advanced into a test position oriented in the flow channel after which it may be further advanced to a disconnect location for removal of the mounting fixture from the passageway. The method includes the step of maintaining a dynamic seal between the test chamber and the mounting chamber during the slidable movement of the mounting way through the passageway.

The preferred method also includes the steps of measuring the pressure of fluid in the flow channel on either side of the heart valve when the heart valve is in the test position and cyclically driving fluid through the flow channel and then measuring the flow rate of fluid as the heart valve opens and closes. The position of the mounting fixture in the first passageway may be automatically monitored to indicate when the mounting fixture is in the passive, test and disconnect positions.

Preferably, a pair of test chambers are provided and a second mounting fixture slides through a passageway in the second test chamber and is provided with a cavity that mounts a second heart valve. A plurality of test fixtures may be employed with each of the test chambers so that a stacked array of mounting fixtures may be used so that successive ones of the mounting fixtures are progressively advanced through its associated passageway. The preferred method further includes the step of maintaining each heart valve in a fluid environment as it is passed from the passive to the disconnect position.

In the preferred form of the present invention, a computer interface and control system is provided so that the preferred method is directed toward a simulated circulatory system that has a flow channel containing a test fluid and which includes a selectably adjustable fluid restriction element in the flow channel, a compensation chamber which provides both an excess fluid compensation reservoir and which may be adjusted to selectively apply pressure to the fluid in the flow channel, and that includes a pulsatile pump having a selectable adjusted period, applitude and duty cycle for driving the fluid in a selected waveform through the flow channel. Accordingly, another embodiment of the preferred method includes the step of providing data processing means for automatically monitoring fluid conditions in the flow channel and adjusting the pressure applied by the fluid restriction element in controlling the waveform of the pump. The data process means is loaded with data corresponding to the desired waveform of the fluid flow through the channel and an initial pressure applied by the fluid restriction element is set to an initial pressure. The pump is then activated through the desired waveform according to its duty cycle. The flow rate of fluid through the flow channel adjacent the heart valve is measured to generate flow rate data, and the pressure of the fluid upstream and downstream of the heart valve is measured to generate channel pressure data. The flow rate data and channel pressure data are input into the data processing means and used to calculate the fluid flow and pressure waveform of the fluid through the flow channel. This actual fluid flow and pressure waveform is then compared with the desired waveform to determine waveform error and the resistance of the fluid restriction element is adjusted by the data processing means to proprotionately reduce the waveform error by interrative processing of the flow rate and the channel pressure data to tune the fluid flow and pressure waveform on successive cycles of the pump until the fluid flow and pressure waveform models the desired waveform within predefined error range. This method may include the step of adjusting the pressure applied by the pressure means as part of the step of reducing the waveform error.

Video recording apparatus may be used in this preferred alternate method wherein the method includes the step of monitoring the visual operation of the heart valve and recording the visual data corresponding to the opening and closing of the valve in order to provide an archival record, and the method may include the step of overlaying recorded visual data with the flow rate data and the channel pressure data.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

I claim:

1. Apparatus adapt to test prosthetic heart valves under flow conditions of a fluid through a flow channel simulating a circulatory system into which the valves are to be used, comprising:

an intake chamber for receiving said fluid having a fluid inlet, a first intake orifice and a second intake orifice;

a first test chamber in fluid communication with said first intake orifice and defining a first test portion of said flow channel, said first test chamber including a first mounting fixture moveably received therein and having a first cavity adapted for securing a first heart valve whereby the first heart valve may be selectively moved from a passive position out of the flow channel and into a first test position interposed in said flow channel, said first mounting fixture having first dynamic sealing means for maintaining a fluid seal with said first test chamber as the first mounting fixture moves therein;

a second test chamber in fluid communication with said second intake orifice and defining a second test portion of said flow channel, said second test chamber including a second mounting fixture moveably received therein and having a second cavity adapted for securing a second heart valve whereby the second heart valve may be selectively moved from a passive position out of the flow channel and into a second test position in said flow channel, said second mounting fixture having first dynamic sealing means for maintaining a fluid seal with said second test chamber as the second mounting fixture moves therein;

a restriction chamber defining a restrictive portion of said flow channel and having first and second restriction chamber flow orifices, said restriction chamber including restriction means for selectively varying resistance to the flow of the fluid through the restriction chamber;

first conduit means for interconnecting said first restriction chamber flow orifice and said first test chamber for fluid flow therebetween and defining a first conduit portion of said flow channel;

second conduit means for interconnecting said second restriction chamber flow orifices and said second test chamber for fluid flow therebetween and defining a second conduit portion of said flow channel;

first fluid pressure compensation means in fluid communication with the flow channel in said first conduit portion for selectively applying pressure to fluid therein and having a first compensation reservoir adapted to receive excess fluid in the flow channel;

second fluid pressure compensation means in fluid communication with the flow channel in said second conduit portion for selectively applying pressure to fluid therein and having a second compensation reservoir adapted to receive excess fluid in the flow channel; and pump means for cyclically pumping fluid alternately by a power stroke and a recovery stroke, said fluid being pumped during the power stroke through said fluid inlet towards said first and second test chambers whereby one of said first and second heart valves passes the fluid therethrough while the other one of said first and second heart valves resists fluid flow, fluid being pumped during the power stroke accumulating under pressure in said first and second compensation reservoirs, and during the recovery stroke whereby said one of the heart valves closes and the other one of the heart valves opens so that said first and second fluid pressure compliance means force fluid through the other one of heart valve back into said intake chamber, said restriction means being selectively adjustable to permit flow of a volume of fluid over a time period of one pump cycle which volume is equal to the volume of fluid displaced by the power stroke of the pump;

said intake chamber, said first and second test chambers, said restriction chamber, and said first and second conduit means forming the flow channel containing fluid for circulation therethrough.

2. Apparatus according to claim 1 including first and second flow meters associated with said first and second conduit means for measuring the velocity of fluid flowing respectively therein and producing first and second velocity flow data signals.

3. Apparatus according to claim 2 including pressure sensor means for monitoring the fluid pressure in said flow path on each flow side of said first and second heart valves.

4. Apparatus according to claim 3 including data processing means for monitoring and processing said first and second velocity flow data signals and said pressure data signals and for controlling the pump means, for selecting the resistance of said restriction chamber and for controlling said first and second compensation means to apply selected pressures on said fluid whereby said fluid flows through the flow channel in a selected flow waveform.

5. Apparatus according to claim 4 including an autonomous wave form generator means receiving waveform data from said data processing means for controlling said pump means whereby said pump means operates to drive the fluid in the selected flow waveform.

6. Apparatus according to claim 4 including video camera and recording means associated with at least some of said optical view ports for storing visual data corresponding to the operation of said first and second heart valves, said data processing means operative to overlay textual waveform data on said visual data for concurrent recording therewith.

7. Apparatus according to claim 1 wherein said flow channel has a fluid charging port and a vent port whereby the flow path can be completely filled with fluid and gases vented therefrom.

8. Apparatus according to claim 7 wherein said first and second test chambers each include a fluid reservoir operative to hold some of said fluid whereby the first and second cavities of said first and second mounting fixtures may be pre-charged with fluid around the first and second heart valves prior to the positioning of the mounting fixtures into the test position so that the cavities do not introduce gases into the flow channel.

9. Apparatus according to claim 1 including a plurality of optical view ports positioned for viewing the opening and closing of said first and second heart valves in the test position during successive power and recovery strokes of said pump means.

10. Apparatus according to claim 9 including video camera and recording means associated with at least some of said optical view ports for storing visual data corresponding to the operation of said first and second heart valves.

11. Apparatus according to claim 10 including optical monitoring means for visually displaying at least some of said visual data.

12. Apparatus according to claim 1 wherein each of said first and second mounting fixture is configured to be mounted in its respective test chamber in at least two rotational positions 180° apart with respect to the axis of rotation whereby the direction of fluid flow through a heart valve mounted therein mey be reversed.

13. Apparatus according to claim 12 wherein said mounting fixtures are cylindrical.

14. Apparatus according to claim 13 wherein said first test chamber has a first passageway formed therethrough intersecting said flow channel from a first entry way to a first exit and said second test chamber has a second passageway formed completely therethrough intersecting said flow channel from a second entryway to a second exit, said first test chamber including a plurality of first test fixtures which may be aligned with one another for successive advancement through said first passageway whereby each first test fixture is moved from the passive position at said first entryway, through the test position and into a disconnect position at said first exit permitting removal thereof from the first test chamber, and wherein said second test chamber includes a plurality of second mounting fixtures which may be aligned with one another for successive advancement through said second passageway whereby each second test fixture is moved from the passive position at said second entryway, through the test position and into a disconnect position at said second exit permitting removal thereof from the second test chamber.

15. Apparatus according to claim 14 wherein each of said first and second test chambers includes a test chamber reservoir at the entryway of its associated said passageway in fluid communication therewith and adapted to contain fluid whereby the first and second cavities of said first and second mounting fixtures, respectively, can be pre-charged with fluid prior to advancement into the test position so that said heart valves are maintained in a fluid environment and introduction of gas into the flow channel avoided.

16. Apparatus according to claim 15 wherein each of said first and second test chambers includes a fixture guide receiving the first and second mounting fixtures as they are respectively advanced out of said first and second exits, said fixture guides defining the disconnect position and operative to fluidly seal said first heart valves in a fluid environment while in the disconnect position.

17. Apparatus according to claim 15 including position sensor means for sensing the position of said first and second mounting fixtures within said first and second passageways, respectively, to signal orientation of the heart valves in the flow channel.

18. Apparatus according to claim 15 wherein each said mounting fixture has leading edge engagement means whereby the leading edge engagement means on one mounting fixture engages the trailing engagement means on a preceeding mounting fixture, for aligning and coupling said mounting fixtures for progressive advancement through the passageway of their respective test chamber, successive mounting fixtures being coupling for corresponding rotation such that rotation of a selected one of the engaged mounting fixtures causes rotation of all mounting fixtures engaged therewith.

19. Apparatus according to claim 18 wherein one of said leading and trailing engagement means comprises male means and the other of said leading and trailing engagement means comprises female means, said male and female means sized for non-rotational mated engagement with one another.

20. In apparatus for testing the operation of a prosthetic heart valve wherein the apparatus includes a flow channel simulating the circulatory system into which the valve is to be implemented, the improvement comprising: a test chamber having a flow channel region extending between a first orifice and a second orifice and adapted for insertion in fluid communication into the flow channel of said apparatus for conducting flow of fluid from one orifice to the other orifice, said test chamber having a passageway therethrough intersecting said flow channel region; a mounting fixture sized for mated engagement in said passageway whereby the mounting fixture may be inserted into an entry opening of said passageway on one side of the test chamber, slideably moved through the passageway and removed from the passageway at an exit opening on another side of said test chamber, said mounting fixture having a cavity extending therethrough and provided with mounting means for mounting and supporting a heart valve to be tested whereby said cavity may be moved into fluid communication with said flow channel region and said heart valve oriented in the flow of fluid through the test chamber; and dynamic sealing means on said mounting fixture for maintaining fluid seal as the mounting fixture is moved through the passageway.

21. The improvement according to claim 20 wherein said test chamber including a fluid reservoir operative to hold some of said fluid whereby the cavity of said mounting fixture may be pre-charged with fluid around the heart valve prior to positioning of the heart valve in the flow of fluid so that the heart valve is maintained in a fluid environment and introduction of gas into the flow channel avoided.

22. The improvement according to claim 20 including a fixture guide receiving said mounting fixture as it is advanced out of said exit opening to define a disconnect position for said mounting fixture, said fixture guide operative to fluidly seal said cavity to maintain the heart valve in a fluid environment while in the disconnect position.

23. The improvement according to claim 20 including seal means on said mounting fixture for circumferentially sealing a leading edge of said mounting fixture and a trailing edge of said mounting fixture, on either side of said cavity, as the mounting fixture is advanced through said passageway so that a longitudinal axial seal is maintained as the mounting fixture slides therethrough.

24. The improvement of claim 23 including a silicon sealing and lubricating material around an outer surface of said mounting fixture between said leading and trailing sealing means, said silicon material operative to facilitate sliding movement of said mounting fixture through said passageway and for preventing fluid leakage around the circumference of said mounting fixture between said trailing and leading sealing means when the mounting fixture is positioned in said flow channel.

25. The improvement according to claim 20 including flow shaping elements mounted on either side of said heart valve in said cavity and operative to shape fluid flow through said heart valve.

26. The improvement according to claim 25 including retaining rings in said cavity for supporting and releasably mounting said heart valve in said mounting fixture.

27. The improvement according to claim 26 wherein at least some of said mounting elements are resilient.

28. The improvement according to claim 20 wherein said passageway is circular in cross-section and said mounting fixture is constructed as a cylinder sized for close fitting, mated engagement with said passageway.

29. The improvement according to claim 28 including a plurality of said mounting fixtures wherein each said mounting fixture has a leading edge engagement means and a trailing edge engagement means whereby the leading edge engagement means on one mounting fixture engages the trailing engagement means on an adjacent mounting fixture for aligning and coupling said plurality of mounting fixtures for progressive advancement through the passageway, successive mounting fixtures being coupled for corresponding rotation such that rotation of a selected one of the engaged mounting fixtures causes rotation of all mounting fixtures engaged therewith.

30. The improvement according to claim 29 wherein one of said leading and trailing engagement means comprises male means and the other of said leading and trailing engagement means comprises female means, said male and female means sized for non-rotational mated engagement with one another.

31. The improvement according to claim 20 including pressure sensor means in said flow channel region on either side of said heart valve when the heart valve is oriented in the flow channel for sensing the pressure of fluid therein and generating a pressure data signal corresponding thereto.

32. The improvement according to claim 20 including position sensor means for sensing the position of said mounting fixture within said passageway to signal orientation of the heart valve in the flow channel.

33. A method for testing prosthetic heart valves by placing a heart valve in a simulated circulatory system defining a flow channel and having adjustable fluid flow rates and pressure, comprising the steps of:
providing at least one test chamber in said flow channel, said test chamber having oppostie test chamber flow orifices whereby fluid may flow from one orifice to the other orifice as part of the flow channel, said test chamber including a first transverse passageway completely therethrough and intersecting said flow channel;
providing a first mounting fixture having a first cavity sized to mount a first heart valve for orientation in the flow channel;
mounting said first heart valve in said first cavity and advancing said first mounting fixture through said first passageway from a passive position wherein said first heart valve is not in said flow channel, through an entryway into the first passageway to a test position wherein the first heart valve is oriented in the flow channel, and to a disconnect location for removal of the first mounting fixture from said first passageway opposite said entryway;
maintaining a dynamic seal between said first test chamber and said first mounting fixture during the movement of the first mounting fixture through the first passageway;
measuring the flow rate of fluid through the flow channel adjacent the heart valve to generate flow rate data; and
measuring the pressure of the fluid upstream and downstream of the heart valve to generate channel pressure data.

34. The method according to claim 33 including the step of cyclically driving fluid through said flow channel with the first heart valve oriented therein and measuring the flow rate of said fluid as the first heart valve opens and closes.

35. The method according to claim 33 including the step of sensing the position of said first mounting fixture in said first passageway and generating a position signal corresponding to orientation of the first heart valve in said flow channel.

36. The method according to claim 33 including the step of providing a second test chamber in said flow channel wherein said second test chamber has opposite test chamber flow orifices whereby fluid may flow from one orifice to the other orifice as part of the flow channel and wherein said second test chamber includes a second transverse passageway completely therethrough and intersecting said flow channel, and providing a second mounting fixture having a second cavity sized to mount a second heart valve for orientation in the flow channel, the method further including the mounting of the second heart valve in the second cavity and advancing the second mounting fixture through the second passageway from a passive position wherein the second heart valve is not in the flow channel, through an entryway into the second passageway to a test position wherein a second heart valve is oriented in the flow channel, and to a disconnect location for removal of the second mounting fixture from the second passageway opposite said second entryway.

37. The method according to claim 33 including the step of providing a plurality of first mounting fixtures each sized for close-fitting, slidable movement through said first passageway and each mounting a respective heart valve, the method further including the step of stacking said plurality of mounting fixtures so that successive ones of said mounting fixtures may be progressively advanced through said first passageway.

38. The method according to claim 33 including the step of maintaining said first heart valve in a fluid environment while it is in the passive position and as it is advanced through said first passageway and while the first mounting fixture is in the disconnect location.

39. A method for testing a prosthetic heart valve oriented at a test location in a simulated circulatory system having a flow channel containing test fluid for circulation, a selectively adjustable fluid restriction element operative to selectively resist flow of fluid through the flow channel, a compensation chamber having a compensation reservoir in fluid communication with the flow channel downstream of the heart valve and a pressure means adapted to selectively and adjustably apply pressure to fluid in the flow channel, and a pump having a selectively adjustable period, amplitude and duty cycle for driving the fluid in a selected waveform through the flow channel, comprising the steps of:
providing data processing means for automatically monitoring fluid conditions in the flow channel and adjusting the pressure applied by the fluid restriction element and controlling the waveform of the pump;
loading said data processing means with data corresponding to the desired waveform of fluid flow through the flow channel;
setting an initial fluid resistance applied by said fluid restriction element;
activating said pump through the desired waveform according to its duty cycle;
measuring the flow rate of fluid through the flow channel adjacent the heart valve to generate flow rate data;
measuring the pressure of the fluid upstream and downstream of the heart valve to generate channel pressure data;
inputting said flow rate data and channel pressure data into said data processing means and calculating the fluid flow and pressure waveform through said flow channel;
comparing the fluid flow and pressure waveform and the desired waveform to determine waveform error; and
adjusting the resistance of the fluid restriction element to proportionally reduce the waveform error by interative processing of the flow rate and channel pressure data to tune the fluid flow and pressure waveform on successive cycles of the pump until the fluid flow and pressure waveform models the desired waveform within predefined error range.

40. The method according to claim 39 including the step of adjusting the pressure applied by the pressure means to reduce the waveform error to tune the fluid flow and pressure waveform within the predefined error range.

41. The method according to claim 40 including the step of monitoring the visual operation of the heart valve as it opens and closes during the cyclical operation of the pump, and the step of video recording visual data corresponding thereto to provide an archival record.

42. The method according to claim 41 including the step of overlaying the recorded visual data with said flow rate data and channel pressure data in a synchronous manner.

* * * * *